United States Patent
Dagher et al.

(10) Patent No.: US 11,360,179 B2
(45) Date of Patent: Jun. 14, 2022

(54) SYSTEMS AND METHODS FOR ESTIMATING MAGNETIC SUSCEPTIBILITY THROUGH CONTINUOUS MOTION IN AN MRI SCANNER

(71) Applicant: The MITRE Corporation, McLean, VA (US)

(72) Inventors: Joseph Dagher, McLean, VA (US); Ben Berman, McLean, VA (US)

(73) Assignee: The MITRE Corporation, McLean, VA (US)

( * ) Notice: Subject to any disclaimer, the term of this patent is extended or adjusted under 35 U.S.C. 154(b) by 0 days.

(21) Appl. No.: 17/084,237

(22) Filed: Oct. 29, 2020

(65) Prior Publication Data

US 2022/0137173 A1    May 5, 2022

(51) Int. Cl.
*G01R 33/565* (2006.01)
*G01R 33/56* (2006.01)
*G01R 33/34* (2006.01)
*A61B 5/055* (2006.01)

(52) U.S. Cl.
CPC ........ *G01R 33/56509* (2013.01); *A61B 5/055* (2013.01); *G01R 33/34092* (2013.01); *G01R 33/5608* (2013.01)

(58) Field of Classification Search
CPC ........ G01R 33/34092; G01R 33/56509; G01R 33/5608
See application file for complete search history.

(56) References Cited

U.S. PATENT DOCUMENTS 8,781,197 B2   7/2014 Wang et al.
9,684,979 B2   6/2017 Lu et al.
(Continued)

FOREIGN PATENT DOCUMENTS

WO   2014/154544 A1   10/2014
WO   2018/165473 A1   9/2018
WO   2019/086284 A1   5/2019

OTHER PUBLICATIONS

Dold et al. (2005) "Prospective Head Motion Compensation for MRI by Updating the Gradients and Radio Frequency During Data Acquisition," Duncan U.S., Gerig G. (eds) Medical Image Computing and Computer-Assisted Intervention—MICCAI 2005. MICCAI 2005. Lecture Notes in Computer Science, vol. 3749. Springer, Berlin, Heidelberg; 8 pages.

(Continued)

*Primary Examiner* — Gregory H Curran

(74) *Attorney, Agent, or Firm* — Morrison & Foerster LLP

(57) ABSTRACT

Systems and methods for estimating magnetic susceptibility of a patient through continuous motion in an MRI scanner are provided herein. In one or more examples, during the collection of data, the patient can be instructed to move their head or other part of the body in a continuous manner and for a fixed duration of time. During the fixed duration of time, magnitude a data from the RF signal can be received by one or more RF coils can be collected. The received and undersampled magnitude data can be converted to phase data which can then be converted to magnetic susceptibility. Thus magnetic susceptibility can be determined while allowing for continuous motion during the MRI scan, which can be more comfortable and feasible for the patient in contrast to techniques that require the patient to hold their body at a particular orientation in the scanner for a fixed duration of time.

36 Claims, 8 Drawing Sheets

(56) References Cited

U.S. PATENT DOCUMENTS

| | | | |
|---|---|---|---|
| 10,061,003 B2 | 8/2018 | James et al. | |
| 2016/0038054 A1* | 2/2016 | Benner | A61B 5/055 600/413 |
| 2019/0033411 A1* | 1/2019 | Katscher | G01R 33/563 |
| 2019/0064302 A1* | 2/2019 | Feiweier | G01R 33/4828 |

OTHER PUBLICATIONS

Wang et al. (2015) "Quantitative Susceptibility Mapping (QSM): Decoding MRI Data for a Tissue Magnetic Biomarker," Magnetic Resonance in Medicine 73; 20 pages.

* cited by examiner

SYSTEMS AND METHODS FOR ESTIMATING MAGNETIC SUSCEPTIBILITY THROUGH CONTINUOUS MOTION IN AN MRI SCANNER

FIELD OF THE DISCLOSURE

The present disclosure relates to systems and methods for recording and estimating magnetic susceptibility of human tissue of a patient using a magnetic resonance imaging (MRI) scanner configured to allow for continuous movement of the patient during a data collection process.

BACKGROUND OF THE DISCLOSURE

Magnetic Resonance Imaging (MM) has been employed in the medical field to provide clinicians within detailed pictures of a patient's anatomy and images of their physiological process. In order to generate an image using MRI, a patient is placed into a chamber (e.g., MRI scanner) that generates a strong magnetic field around the patient. The magnetic field can cause hydrogen atoms within the patient's body to emit a radio frequency (RF) signal which can be detected by one or more RF receiving coils that are part of the MM scanner. The magnitude and phase of the RF signal can be used to create an image of the internal anatomy and physiological processes occurring within the body.

Clinicians traditionally have been interested in using the magnitude information provided by an MRI scan to build detailed images of a patient's anatomy for the purposes of assessing and diagnosing a myriad of conditions. The magnitude of a received RF signal can be used to determine the precise location, position, and condition of organs and other structures within a patient's body. Thus, the magnitude information provided by an MRI scan can be used to provide detailed internal images of the body.

While magnitude information can provide useful information to a clinician, the phase information produced by an MRI scan also provide useful information about the patient being scanned. For instance, the phase information generated from an MRI scan can be used to measure the magnetic susceptibility of the tissue in the human body. The magnetic susceptibility of various tissues in the human body can be used to determine the amount and concentration of various molecules in the human body such as iron, heme, copper, and oxygen and can also provide information regarding the temperature, flow, tissue elasticity, and molecular content of the tissue being analyzed. Accurately recording the amount of concentration of various molecules in the human body can provide clinicians with a powerful tool to diagnose and treat patients with various pathologies.

However, deriving molecular composition from an MRI phase signal can be a difficult process. Generally, the first step involves calculating magnetic susceptibility from the MRI data. This is an ill-posed problem which requires injecting prior information in order to generate artifact-free images of tissue magnetic susceptibility. Various approaches to 'regularize' this process are known to yield vastly different solutions. The gold standard in the in vivo mapping of magnetic susceptibility of tissue is a long and labor-intensive MRI scan which requires acquiring the same scan at different fixed head positions. The subject is expected to remain still, while holding this pre-determined head position, for the duration of the MRI scan. Patients with various disorders (particularly those with neurological disorders) generally cannot be expected to move their body into fixed positions and hold still for long periods of time. Generally, movement during any MRI scan leads to measurement errors. Together with the long acquisition time needed to obtain reliable magnetic susceptibility information, requiring patients to be motionless during an MRI scan further erodes the current ability to use magnetic susceptibility information as a diagnostic tool.

What is needed is an MRI scanner and method for use of the scanner that can collect sufficient and reliable magnetic susceptibility information from a patient in a manner that doesn't require the patient to engage in inviable and burdensome collection procedures.

SUMMARY OF THE DISCLOSURE

Accordingly, systems and methods for estimating magnetic susceptibility of a patient through continuous motion in an MRI scanner is provided. In one or more examples, the MRI scanner can be configured with a pulse sequence protocol that can allow for measurements of off-resonance effects as well as motion tracking hardware that can be used to track the users motion in the scanner as a function of time. In one or more examples, during the collection of data, the patient can be instructed to move their head or other part of the body in a continuous manner and for a fixed duration of time. During the fixed duration of time, both magnitude and phase data from the RF signal received by one or more RF coils can be collected.

In one or more examples, the data collected during the MRI scanning procedure can be organized into one or more "bins" that are created based on the motion registration of the patient. (i.e., the range of motion that the user moved during the scanning procedure). Each bin can represent a narrow range of positions in two or more dimensions.

In one or more examples, the phase information for each bin can be calculated by using not only the data points contained within a particular bin, but also data points that are found in adjacent bins, thereby providing sufficient data to overcome the loss of the collected phase data. Once the phase information for each bin has been calculated, the information can be used to calculate the magnetic susceptibility of tissue within the patient thereby providing the clinician with useful information that might have not been available with magnitude based MM imaging.

DETAILED DESCRIPTION

Figure 1:
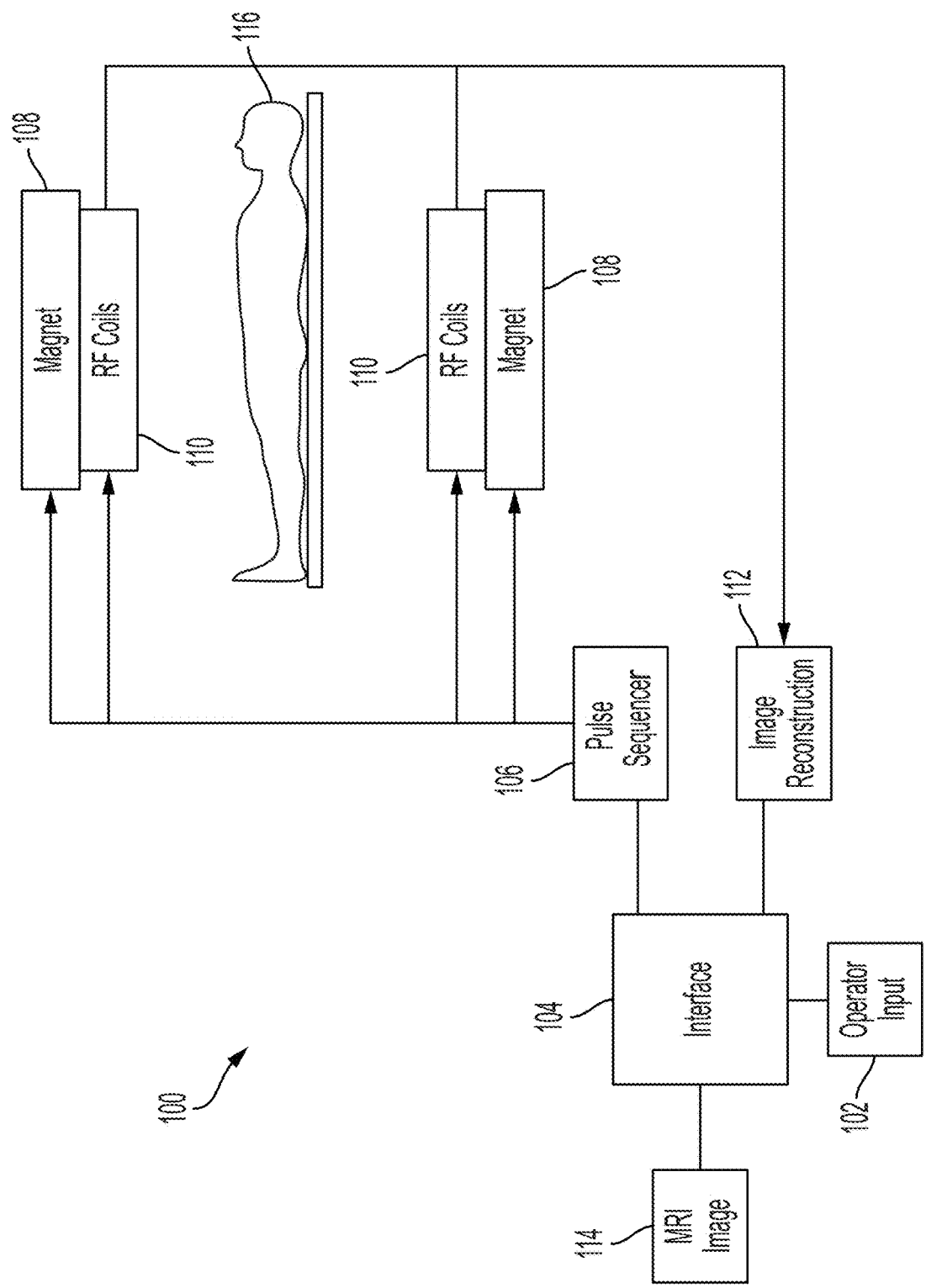
FIG. 1 illustrates an exemplary MRI system according to examples of the disclosure.

In the following description of the disclosure and embodiments, reference is made to the accompanying drawings in which are shown, by way of illustration, specific embodiments that can be practiced. It is to be understood that other embodiments and examples can be practiced and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes," "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Some portions of the detailed description that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic, or optical signals capable of being stored, transferred, combined, compared, and otherwise manipulated. It is convenient at times, principally for reasons of common usage, to refer to these signals as bits, values, elements, symbols, characters, terms, numbers, or the like. Furthermore, it is also convenient at times to refer to certain arrangements of steps requiring physical manipulations of physical quantities as modules or code devices without loss of generality.

However, all of these and similar terms are to be associated with the appropriate physical quantities and are merely convenient labels applied to these quantities. Unless specifically stated otherwise as apparent from the following discussion, it is appreciated that, throughout the description, discussions utilizing terms such as "processing," "computing," "calculating," "determining," "displaying," or the like refer to the action and processes of a computer system, or similar electronic computing device, that manipulates and transforms data represented as physical (electronic) quantities within the computer system memories or registers or other such information storage, transmission, or display devices.

Certain aspects of the present invention include process steps and instructions described herein in the form of an algorithm. It should be noted that the process steps and instructions of the present invention could be embodied in software, firmware, or hardware, and, when embodied in software, could be downloaded to reside on and be operated from different platforms used by a variety of operating systems.

The present invention also relates to a device for performing the operations herein. This device may be specially constructed for the required purposes, or it may comprise a general-purpose computer selectively activated or reconfigured by a computer program stored in the computer. Such a computer program may be stored in a non-transitory, computer-readable storage medium, such as, but not limited to, any type of disk, including floppy disks, optical disks, CD-ROMs, magnetic-optical disks, read-only memories (ROMs), random access memories (RAMs), EPROMs, EEPROMs, magnetic or optical cards, application-specific integrated circuits (ASICs), or any type of media suitable for storing electronic instructions and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

MRI technology has been used extensively to provide clinicians with detailed images of the internal structures of the human body as well as physiological processes occurring within the body. Images generated by MRI technology can be more detailed and precise than images generated by other technologies such as X-ray, thus allowing clinicians to make more precise and accurate diagnoses of various diseases and conditions.

The use of MRI technology to image the human body can include generating a magnetic field that causes the hydrogen atoms within the tissue being imaged to orient themselves with the magnetic field. Specifically, an oscillating magnetic field at a specific frequency (i.e., resonance frequency) is applied to an area to be imaged. When applied at the resonance frequency the magnetic field causes some of the hydrogen atoms to align with the magnetic field, and causes some of the hydrogen atoms to align in opposition to the magnetic field. Once the hydrogen atoms in the tissue being imaged have been aligned by the magnetic field, the MRI scanner will transmit one or more RF signals to the tissue being imaged. The RF signals can be absorbed by the hydrogen atoms that are aligned in opposition to the magnetic field, causing the hydrogen atoms to then become aligned with the magnetic field. Once the RF signal is removed, the hydrogen atoms whose alignment was flipped by the RF signal, will return to their original orientation (i.e., in opposition to the magnetic field) and in turn will give off RF energy that can be detected by one or more RF receiving coils in the MRI scanner. The magnitude of the RF signals detected by the RF coils can be proportional to the amount of tissue in a given area, and the MRI scanner can use this information to create detailed images of the area being scanned.

FIG. 1 illustrates an exemplary MRI system according to examples of the disclosure. The system 100 of FIG. 1 illustrates an exemplary system configured to generate MRI images by a clinician. In the example of FIG. 1, a subject 116 (the patient to be imaged) can be placed within a chamber that includes one or more magnets 108 and one or more RF coils 110. The one or more magnets 108 can be communicatively coupled to a pulse sequencer 106. In one or more examples, the pulse sequencer 106 can be configured to control the one or more magnets 108 so as to generate a magnetic field in a particular area of the subject 116 that is desired to be imaged. The pulse sequencer 106 can be configured to generate a magnetic field at the desired frequency so as to cause the hydrogen atoms in the tissue being examined to orient themselves with respect to the magnetic field.

In one or more examples, the one or more RF coils 110 can be also communicatively coupled to pulse sequencer 106. The one or more RF coils 110 can be configured to both transmit and receive RF pulses. In one or more examples, the pulse sequencer 106 can be configured to cause the one or more RF coils 110 to transmit RF pulses directed at the tissue being imaged so as to cause the one or more hydrogen atoms that are aligned in opposition to the magnetic field to absorb the energy provided by the RF pulses so as to cause their orientation to flip so as to become aligned with the magnetic field.

In one or more examples, the one or more RF coils 110 can be also communicatively coupled to an image reconstruction unit 112 that can be configured to receive the signals received by the one or more RF coils 110. As discussed above, when the hydrogen atoms whose orientation has been flipped due to the RF pulses due to energy absorption return to their original orientation thereby giving off RF energy, the RF coils can receive the energy being expelled from the hydrogen atoms. In one or more examples, the image reconstruction unit 112 can be configured to collect the RF signals provided by the one or more RF coils 110 and use the received signal to construct an image of the tissue being analyzed.

In one or more examples of the disclosure, both the pulse sequencer 106 and the image reconstruction unit 112 can be communicatively coupled to an interface 104. The interface 104 can facilitate the exchange of information between the components of the MRI system and an operator of the MRI system. In one or more examples, the interface 104 can receive inputs 102 from a human operator of the MRI system. Inputs can include setting various operating parameters such as specific pulse sequences that the MRI system will generate during its operation. The interface 104 can also provide output data to the operator of the MRI system. In one or more examples, the interface 104 can generate a visualization of the MRI image produced by the image reconstruction unit 112 which can then be used by a clinician to diagnose and treat a patient.

The signal received by each RF coil 'c' 110 can be represented using the following equation:

$$I_c(r) = T_c(r)m(r)e^{i\varphi(r)} \quad \text{(equation 1)}$$

In equation 1 above, r represents the spatial coordinates, m(r) can represent the magnitude of the image, and φ(r) can represent the phase of the image and $T_c(r)$ is the complex sensitivity of the RF coil 'c'. Conventionally, MRI images are primarily concerned about the magnitude of the signal rather than the phase of the signal. The majority of images analyzed currently by MRI users (e.g., clinicians, radiologists) are magnitude-domain images. Because the magnitude of the signal can be proportional to the density of the tissue at a particular location, magnitude-domain images can be very useful to help visualize both the anatomy and physiological processes that exist in the imaged area.

Phase information can also be useful to a clinician. In one or more examples, the received RF signals can arrive when they are expected to, while other RF signals can arrive with a delay which is captured in the phase information. The delay in receiving a signal (i.e., phase distortion) can indicate to a clinician that the tissue from which the RF signal was received was resonating slightly out of frequency from other tissue surrounding it. The delay can be caused by various phenomenon occurring within the tissue being examined. For example, if there is a micro-bleed occurring in the tissue being examined then the tissue may contain excess blood. Blood contains iron, hemoglobin, or more oxygen that can disturb the magnetic field locally in the area being examined. In one or more examples, the off-resonance effect caused by phenomenon such as a micro-bleed may not be captured clearly by examining the changes in magnitude of a signal, but instead may be captured more accurately in the phase information of a given signal.

Phase information can be used to determine the magnetic susceptibility of tissue, which can be a useful metric that gives clinicians information that they can use to treat and diagnose patients. Magnetic susceptibility analysis can be used to determine iron content in blood, calcification of tissue, oxygenation of tissue, and other phenomenon. In MRI images that are based on the magnitude of the signal, the phase information is often discarded thus losing valuable information relating to the magnetic susceptibility of tissue.

The transformation from susceptibility of tissue to phase data as obtained by an MRI scanner is a lossy process. In one or more examples, the phase information acquired during the MRI scan is first converted into a measurement of the local magnetic field. Specifically, the relationship between the local field and the phase information received by an MRI scanner can be characterized by equation 2 provided below.

$$\delta B(r) = \frac{\phi(r)}{2\pi\gamma TE} \quad \text{(equation 2)}$$

In equation 2 above, a (r) can represent the change in the magnetic field flux density, φ(r) can represent the phase information received by an MRI scanner, TE can represent the echo time which the measurement is made, and γ is the gyromagnetic ratio.

The total magnetic field flux can have two different contributions. We write these contributions in equation 3 below.

$$\delta B(r) = \delta B_\chi(r) + \delta B_0(r) \quad \text{(equation 3)}$$

The first contribution to δB(r) on the right side of equation 3, $\delta B_\chi(r)$, is the field caused by magnetic susceptibility variations (such as the spatial variations in tissue magnetic susceptibility over the brain), and $\delta B_0(r)$ is an unknown spatially varying global frequency component, which is due to factors such as coil offset, magnetic field imperfections, etc.

The magnetic field offset $\delta B_0(r)$ contains no information about the desired tissue magnetic susceptibility. The effects of $\delta B_0(r)$ can thus be removed through one of two different approaches. The first is a pre-processing step, normally referred to as Background Field Removal. The objective of Background Field Removal is essentially to extract $\delta B_\chi(r)$ from total magnetic field δB(r) and thus feed $\delta B_\chi(r)$ to the following magnetic susceptibility inversion step. The second approach to removing the effects of $\delta B_0(r)$ is through a single step process, inherent to magnetic susceptibility reconstruction, as proposed below.

The relationship between changes in the local field and magnetic susceptibility can be characterized by equation 4 below:

$$HX=\Delta B_\chi \quad \text{(equation 4)}$$

In equation 4 above, $H_\theta$ is the known dipole kernel associated with patient's head position θ, and $\Delta B=F(\delta B_\chi)$, where F is the Fourier Transform operator. In one or more examples, the dipole kernel may not be an invertible process in that it destroys information (zeros in the frequency domain) about the magnetic susceptibility that can be difficult to recover without making prior assumptions about the object being scanned. This phenomenon can be made more difficult due to noise. Thus, solving for magnetic susceptibility can be referred to as an "ill conditioned problem."

The goal is to calculate the magnetic susceptibility of the tissue χ from $\Delta B_\chi$. This task can be represented using equations 5 & 6 below, where $H^{-1}$ is the inverse of the dipole operator and $F^{-1}$ is the inverse Fourier Transform operator:

$$X=H^{-1}(\Delta B_\chi) \quad \text{(equation 5)}$$

$$X=F^{-1}(X) \quad \text{(equation 6)}$$

Various solutions to the ill-conditioned inverse problem in equation 5 have been proposed. They range from single-step approaches to multi-step iterative solutions that heavily rely on injecting prior-knowledge about the object, regularization, and other assumptions. The resulting solutions are often biased, inconsistent and suffer from artifacts.

Alternatively, another approach to solve for the magnetic susceptibility of the tissue χ is to acquire MRI data at "n" different angles of the head. This requires the patient to hold their head still for n different acquisitions, which require n times longer than 1 acquisition. The main motivation behind this approach is the collection of the n different dipole kernels constitute an invertible and well-conditioned operation that could be more easily inverted in post-processing. Namely, the intersection of the null-space between the n different kernels is chosen to be as small as possible. This operation can be described by Equation 7.

$$\begin{bmatrix} H_1 \\ \vdots \\ H_n \end{bmatrix} X = \begin{bmatrix} \Delta B_{\chi_1} \\ \vdots \\ \Delta B_{\chi_n} \end{bmatrix} \quad \text{(equation 7)}$$

Where $H_i$ is the dipole kernel associated with each of the positions of the patient's head and $\Delta B_{\chi_i}$ is the resulting field measured at that position.

A solution to equation 7 exists as long as a sufficient number and range of angles are acquired. One such MRI procedure exists and is known as Calculation of Susceptibility through Multiple Orientation Sampling (COSMOS). The COSMOS procedure can generate mathematically sufficient data by oversampling the magnetic field (and thereby the phase) from multiple orientations. In other words, the COSMOS procedure can generate mathematically sufficient data to determine magnetic susceptibility of a tissue by taking multiple snapshots of the magnetic field at multiple orientations relative to the tissue being analyzed.

Figure 2:
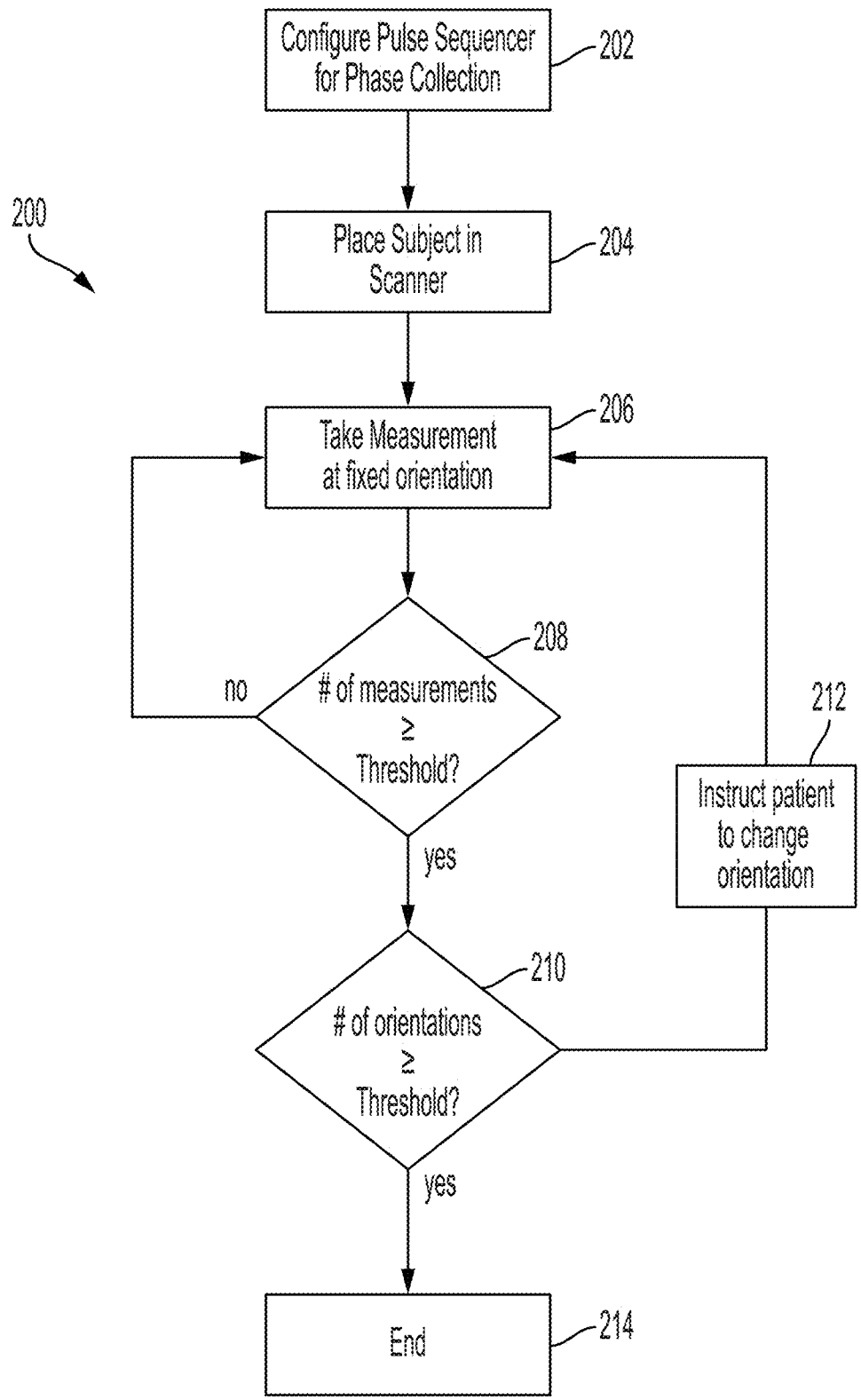
FIG. 2 illustrates an exemplary process for obtaining a phase image from an MRI scanner according to examples of the disclosure.

FIG. 2 illustrates an exemplary process for collecting phase data from an MM scanner according to examples of the disclosure. In the example of FIG. 2 process 200 can represent a procedure that an MRI scanner operator uses to extract sufficient phase information for a tissue sample, so as to accurately determine its magnetic susceptibility. In one or more examples, the process 200 can begin at step 202 wherein an operator of the MRI scanner can configure a pulse sequencer (described above with respect to FIG. 1) to generate a pulse sequence that facilitates the optimal collection of phase data. In one or more examples, a pulse sequence protocol used to generate magnitude-domain images may be different than a pulse sequence protocol meant to generate magnetic susceptibility images or measurements. Thus, in order to configure the device to generate magnetic susceptibility measurement, in one or more examples, the operator, prior to beginning data acquisition, may need to adjust the pulse sequence protocol administered by the pulse sequencer so as to optimize it for phase collection. Additionally, in one or more examples, a pulse sequence protocol can be configured not only to optimize it for phase collection but to also configure it to optimize it to collect data from a particular portion of the patient's body such as the brain or the heart. In other words the pulse sequence protocol used to collect phase images of the brain may be different than the pulse sequence protocol used to collect phase images of the heart. Specifically, cardiac pulse sequences have to be motion gated or motion corrected, and often times triggered by a physiological monitoring tool such as a cardiac pulse, or electrocardiogram.

Once the pulse sequence protocol has been configured so as to collect phase data at step 202, the process can move to step 204 wherein a subject (i.e., a patient) is placed into a scanner. In one or more examples, at step 204, the patient can be placed within the scanner at a particular orientation depending on the desired portion of the body to be scanned. For instance, if the area of interest is the brain, then at step 204 when the patient is placed in the scanner, they can be placed in the scanner so that their head is positioned at a particular orientation. For instance, in one or more examples, the head can be tilted to one side (i.e., tilted towards one shoulder the other, or tilted up or down) in a particular orientation. Once the subject has been placed at the desired orientation at step 204, the process 200 can move to step 206 wherein an MRI measurement is taken at the fixed orientation. Taking an MRI measurement can include generating the appropriate magnetic field and RF signals and receiving the RF signals being released by the hydrogen atoms in the tissue being studied. In one or more examples, the pulse sequencer configured at step 202 can be used to generate and receive the appropriate signals by coordinating the actions of each of the components in the MRI scanner.

In one or more examples, and as described above, in order to generate enough measurements so as to solve the inverse problem, a single orientation measurement may not be adequate to ensure that the MRI data is mathematically sufficient to reconstruct an accurate estimate of the magnetic susceptibility. Thus, in one or more examples, in order to generate such sufficient data, measurements may have to be acquired at different orientations.

In addition to collecting enough orientations, enough measurements must be collected per orientation in order to generate such mathematically sufficient set. Traditional MM protocols must collect all k-space data within a specific region in the Fourier domain in order to generate an image (magnitude or phase) at a particular resolution. Thus, in one or more examples, once a measurement at the fixed orientation is acquired at step 206, the process 200 can move to step 208, wherein a determination is made as to whether the number of measurements taken at the fixed orientation of step 206 is equal to or greater than a pre-determined threshold. If it is determined that the number of measurements is not equal to or greater than the pre-determined threshold, then the process can revert back to step 206 to take an additional measurement at the same orientation. If however the number of measurements at the fixed orientation is equal to or greater than the pre-determined threshold, then the process can move to step 210 described in detail below. In one or more examples, the predetermined threshold of step 208 can be selected so as to ensure that the number of measurements are adequate to provide mathematically sufficient data so as to solve the inverse problem and thus solve for the magnetic susceptibility of the tissue being imaged by the MRI scanner.

After ensuring that an adequate number of measurements has been taken at a particular orientation at step 208, the process 200 can move to step 210 wherein a determination can be made as to whether data has been collected at sufficient orientations so as to provide an adequate set of data to solve for magnetic susceptibility. Specifically, at step 210 a determination can be made as to whether data has been collected from a predetermined number of orientations (i.e., a threshold). If it is determined at step 210 that measurement data has been taken from an adequate number of orientations, then the process can move to step 214 wherein it is terminated. Otherwise, if it is determined that there are not an adequate number of orientations so as to determine the magnetic susceptibility of the tissue being analyzed, then the process can revert to step 212 wherein the patient is instructed to change their orientation. In the examples of a brain scan, the patient can be told to orient their head in a different orientation by changing the way they are tilting their head. In one or more examples, once the patient has changed their orientation at step 212, the process 200 can move back to step 206 wherein a measurement is taken at the new orientation.

As illustrated by the process 200 of FIG. 2, the process of obtaining sufficient MRI data to calculate magnetic susceptibility can require the patients to not only position their body in a plurality of fixed positions, but can also require that the patient hold their body in a particular orientation for a fixed duration of time so that enough measurement data can be collected. These requirements can mean that the patient has to hold their body in an uncomfortable position for long periods of times, and may even have to orient their body in a variety of positions so as to acquire the required data. Thus, the process described above with respect to FIG. 2 may not be clinically viable as it places the patient under too much duress and discomfort during the MRI scan. In one or more examples, the number of fixed orientations can be 12 or more and the time required at each orientation to acquire enough data can take five to ten minutes, thus requiring a procedure that can take up to an hour and require the patient to maintain a fixed position for long periods of time.

Because the process described above with respect to FIG. 2 can require a great deal of time and uncomfortable positioning, many methods for determining the magnetic susceptibility of tissue can approximate the magnetic susceptibility of tissue using only a single fixed position but making assumptions about the original object. However, the assumptions can lead to large measurement errors or artifacts in the generated image that may be unacceptable.

In light of the limitations described above with respect to FIG. 2, what is needed is a process that is both comfortable to the patient while at the same time generating accurate magnetic susceptibility estimates. As described in further detail below, generating adequate data to determine the magnetic susceptibility of tissue without requiring the patient to engage in a long and uncomfortable data acquisition process can require an adjustment to the architecture of the MRI scanner, a change in the method to collecting data from a patient, as well as an adjustment to the method in which the data acquired by the scanning process is used to solve for magnetic susceptibility.

Figure 3:
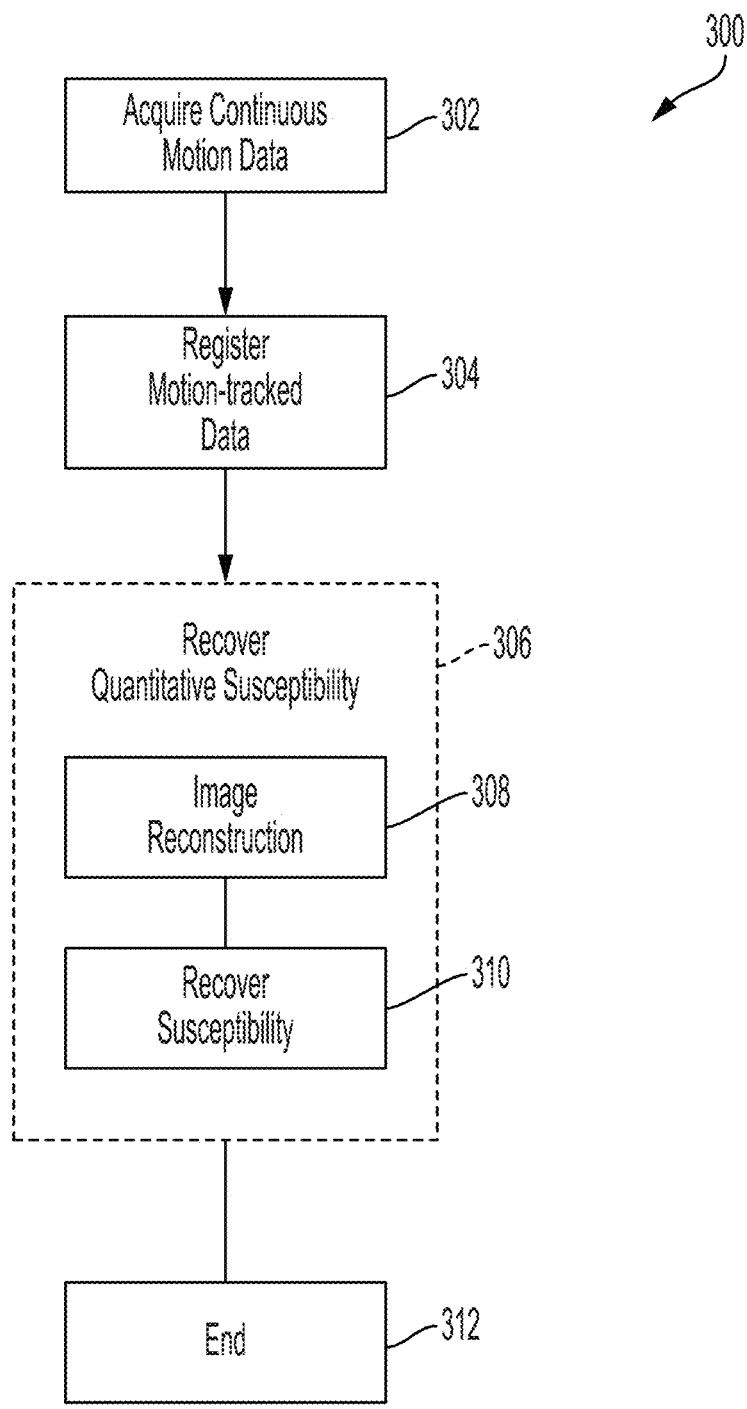
FIG. 3 illustrates another exemplary process for obtaining a phase image from an MRI scanner according to examples of the disclosure.

FIG. 3 illustrates another exemplary process for obtaining a phase image from an MRI scanner according to examples of the disclosure. FIG. 3 illustrates a process 300 by which an MRI scanner can be used to generate data while allowing for the patient to engage in continuous motion during the collection process, and use the generated data to determine the magnetic susceptibility of the tissue being scanned.

In one or more examples of the disclosure, the process 300 can begin at step 302 wherein the patient is instructed to continuously move one or more parts of their body (such as their head) while the MRI scanner obtains measurements from the patient while they are continuously moving. As will be described below with respect to FIG. 4, the MRI device can be configured to include one or more components that track the movements of the user's body such that the exact position of the user's body can be known and associated with the one or more measurements taken with the scanner.

In one or more examples of the disclosure, after acquiring MRI data from a patient continuously moving during the scanning process at step 302, the process can move to step 304 wherein the acquired data can be "registered." In one or more examples, "registering" can refer to the process of associating each MRI data point with a position of the user's body, and then placing the MRI data point (with the known position) into one or more bins for use in reconstructing a phase image. By registering each data point (i.e., associating it with a measured orientation of the user's body) the obtained data can be associated with motion taken from the patient's frame of reference rather than the scanner's frame of reference (described in further detail below).

Once each data point has been registered at step 304, the process 300 can move to step 306 wherein the registered data can be used to recover the quantitative magnetic susceptibility of the tissue being sampled. In one or more examples, step 306 can include two additional steps 308 and 310. In order to recover the magnetic susceptibility at step 306, a phase image of the tissue being scanned can be reconstructed using the registered motion-tracked data acquired at step 304 (described in further detail below). As described in further detail below, in order to create the phase image reconstruction, the process 300 at step 308 can use the registered data that is placed into one or more bins based on the position of the user's body to reconstruct a phase image of the tissue being scanned. A particular method of recovering magnetic susceptibility is provided below, however the disclosure should not be seen as limited to the example, and other methods of recovering magnetic susceptibility from MRI data acquired during a continuous scan may be applicable. For example, in one or more examples, recovering the quantitative susceptibility can include a single step method that can jointly combine undersampled phase and magnitude data over angles/time into one magnetic susceptibility volume. In one or more examples of the disclosure, recovering the quantitative susceptibility can include using a machine learning approach that can cake in MRI data and generate a magnetic susceptibility volume. In one or more examples of the disclosure, recovering the quantitative susceptibility can include using phase image across all collected angles and turning the phase images into a collection of phase images across a subset of angles (synthetic angles not necessarily encountered during collection) and then reconstructing the resulting images into one magnetic susceptibility volume.

In one or more examples (and described in detail below), once a phase image has been reconstructed at step 308, the reconstructed phase image can be used to recover the magnetic susceptibility of the tissue, as described below in more detail. Step 310 should be understood as an exemplary application of using the generated phase image acquired at step 308 and should not be seen as limiting. In one or more examples, the phase image generated at step 308 using data that is acquired by continuous motion of the patient can be used for other purposes without departing from the scope of the disclosure. In the example of FIG. 3, after recovering the magnetic susceptibility of the tissue at step 310, the process can move to step 312 wherein the process 300 is terminated.

As discussed above with respect to FIG. 2, in order to generate mathematically sufficient data to provide accurate magnetic susceptibility measurements, data may need to be acquired at multiple orientations. However, in order to alleviate the issues with requiring data to be acquired at fixed positions, it can be more viable to have the patient move their body in a continuous manner thereby reducing the strain on the patient. However, instructing a patient to move their body in a continuous manner can present challenges for generating a phase image. In the example of FIG. 2, the patient can be instructed to move their body into a very specific position thereby allowing the MRI operator to know the exact position of the body at any given time within a reasonable degree of certainty. However, if the patient is asked to move their body continuously, the exact position of the body and any given moment in time may not be accurately known. Thus, in one or more examples, the MRI scanner architecture described above with respect to FIG. 1 can be modified so as to provide the device with accurate information as to the orientation of the body at any given moment of time during the data acquisition process.

Figure 4:
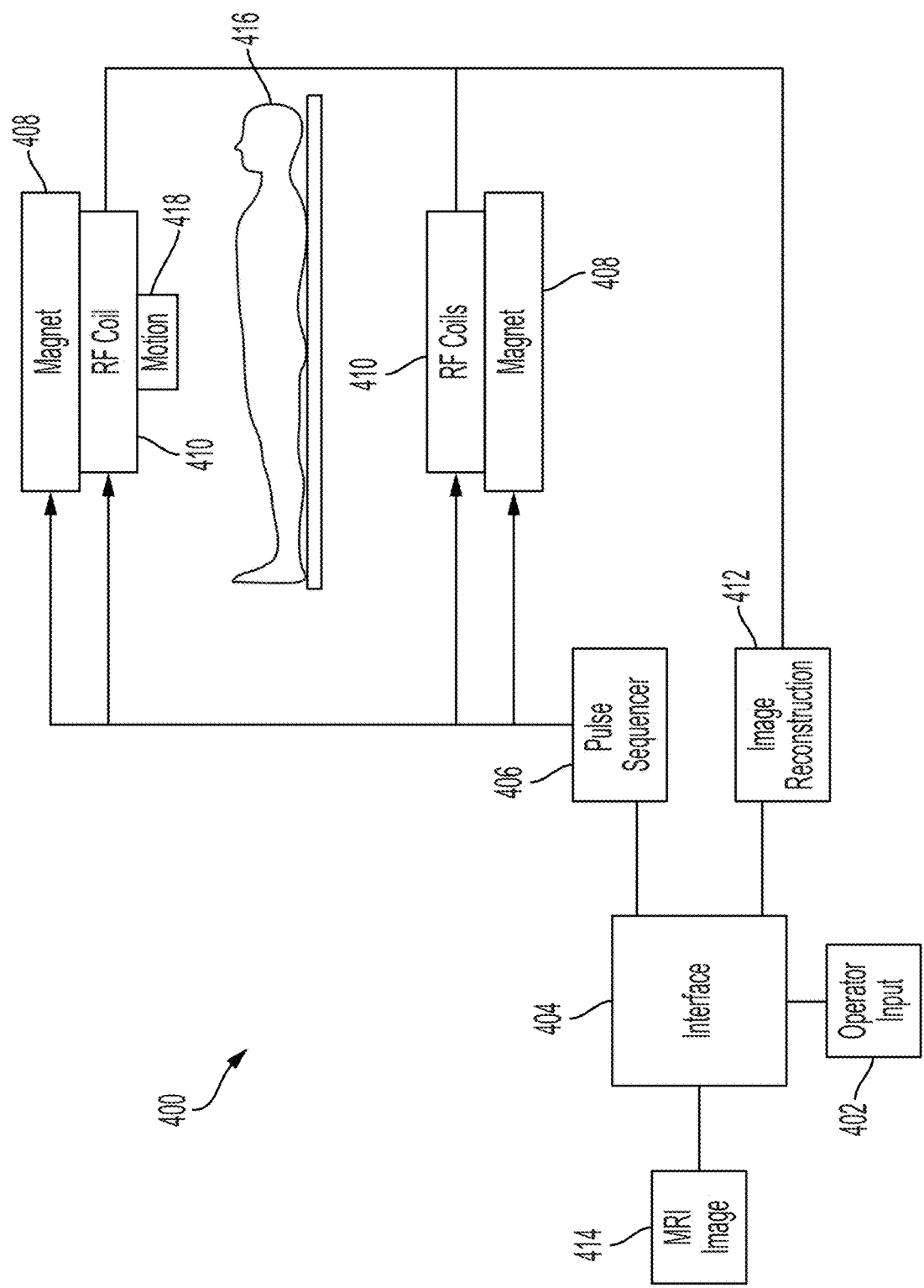
FIG. 4 illustrates MRI system configured to acquire magnetic susceptibility of tissue within a patient according to examples of the disclosure.

FIG. 4 illustrates a MRI system configured to acquire magnetic susceptibility of tissue within a patient according to examples of the disclosure. In the example of FIG. 4, MRI system 400 can include substantially the same components as the MRI system 100 of FIG. 1. In one or more examples, components 402, 404, 406, 408, 410, 412, and 414 can operate in substantially the same manner as their counterparts 102, 104, 106, 108, 110, 112, and 114 respectively, and thus the description above with respect to the components of FIG. 1 can be referenced for a description of their operation. In one or more examples, the pulse sequencer 406 can be configured with a pulse sequence protocol that is configured to obtain accurate phase data from the MRI scanner. Furthermore in one or more examples, and as described in further detail below, image reconstruction unit 412 can be configured to calculate magnetic susceptibility from data generated through continuous movement of the patient so as to produce accurate magnetic susceptibility measurements.

In one or more examples, MRI system 400 can additionally include a motion tracker 418 which can track the motion of a patient 416 in the scanner. Specifically, motion tracker 418 can be configured to track the orientation of a patient's body or portion of the body (such as the head) and any given moment in time. Thus, in one or more examples, motion tracker 418 can generate data that indicates what the orientation of the body was as a function of time. As will be discussed in further detail below, the data generated by the motion tracker 418 can be used to process the MRI data so as to generate accurate magnetic susceptibility readings. In one or more examples, the motion tracker can include a camera that can be configured to track the body part of interest (such as the head), and determine the position of the head at any given moment in time. In one or more examples, the motion tracker can be configured to read one or more magnetically sensitive barcodes that are applied to the patient that can show up in the image taken from the camera and be used to determine the position of the body part at any given moment in time. Generally, the motion tracker 418 can be configured to give the MRI scanner the position of the body part at any given moment in time within a reasonable degree of accuracy.

The system architecture provided by FIG. 4 can allow for a simpler and patient friendly data collection process. By modifying the MRI scanner with respect to its pulse generation sequence and the addition of motion tracking, the process of collecting data can be simplified so that it does not require the patient to orient their body in awkward or uncomfortable positions for long periods of time. Specifically, the modified MRI scanner can allow for the patient to continuously move their head during the data acquisition phase of the procedure which can be more comfortable for the patient, take less time than previous phase collection process, and produce magnetic susceptibility images that can me more accurate than conventional MM phase scans.

Figure 5:
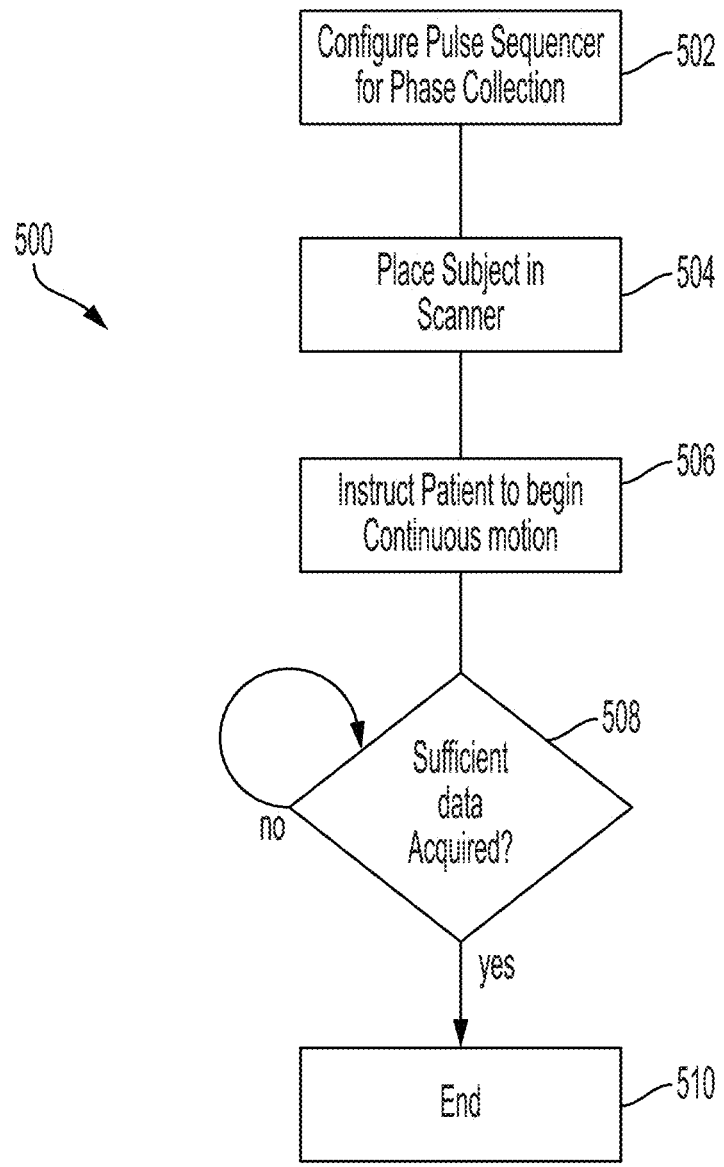
FIG. 5 illustrates an exemplary method of collecting data from an MRI system configured to acquire magnetic susceptibility of tissue within a patient according to examples of the disclosure.

FIG. 5 illustrates an exemplary method of collecting data from an MRI system configured to acquire magnetic susceptibility of tissue within a patient according to examples of the disclosure. In the example of FIG. 5, the process 500 described below can be utilized in an MRI system that has been configured to generate magnetic susceptibility data from a patient as described above with respect to FIG. 4. The process 500 of FIG. 5 can begin at step 502 wherein the pulse sequencer unit of the MRI device is programmed by an operator with a pulse sequence that is configured to collect MRI phase data. In one or more examples, the pulse sequence generated by the pulse sequence generator can be robust to motion and enable a retrospective binning of the data (as will be further described below.) Furthermore in one or more examples, the specific pulse sequencer can be dependent on the body part being imaged. Thus, while one pulse sequence can be used to generate phase images of the brain, a different pulse sequence may need to be configured to take phase images of the heart.

Once the pulse sequencer has been configured at step 502, the process 500 can move to step 504 wherein the patient is placed into the MRI scanner. In one or more examples, the precise position of the patient when they enter the scanner may not be important as the patient will ultimately continuously move during the scanning procedure and thus is not required to maintain a fixed position during the scanning process.

After the patient has been placed into the scanner at step 504, the process 500 of FIG. 5 can move to step 506, wherein the patient is instructed to begin continuously moving one or more portions of the body that are being scanned. Using the human head as an example, at step 506 the patient can be instructed to move their head up and down and left to right in a continuous manner. In one or more examples, continuously moving the head can include tilting the head up and down and left to right in any direction that the patient desires at any moment of time, thus giving the patient flexibility to control their own movement without requiring any substantial coaching or instruction from the MRI operator.

Once the patient begins the continuous motion at step 506, the process 500 can move to step 508 wherein a determination is made as to whether the pulse sequence protocol has been completed thereby allowing for sufficient data (described in further detail below) to be acquired to determine magnetic susceptibility. If at step 508, the pulse sequence protocol has been completed and sufficient data has been acquired then the process 500 can move to step 510 wherein the process is terminated. If however, at step 508 it is determined that the sufficient data has not been acquired, then the process 500 can wait at step 508 until it is determined that sufficient data has been acquired.

In comparing and contrasting the method of MRI phase data acquisition described in FIG. 2 with the example described in FIG. 5, it can be readily apparent that the example described with respect to FIG. 5 can be more efficient from a time perspective, and can be more comfortable from a patient's perspective. Rather than having to place a patient's body in specific orientations and hold the orientation for a long duration time, the process of FIG. 5 can allow the patient to continuously move the body part being imaged and for a shorter duration of time than the process described above with respect to FIG. 2.

In order to have a mathematically sufficient data set to calculate magnetic susceptibility, the collection method described above with respect to FIG. 5 can be modified to ensure that there is mathematically sufficient data to solve the inverse problem of magnetic susceptibility. Since the method of FIG. 5 may not require the patient to move and hold their body in specific orientations, a modified technique to processing the data can be employed to ensure that accurate magnetic susceptibility images are rendered even though the data at a particular orientation may be sparse, i.e., the k-space data at the desired resolution have not been fully sampled/collected. Because the patient is moving continuously and in varied orientations, the acquired data can be categorized spatially rather than temporally, and data that is spatially close to one another can be used to provide a mathematically sufficient data set so as to accurately calculate the magnetic susceptibility of tissue being analyzed.

Figure 6:
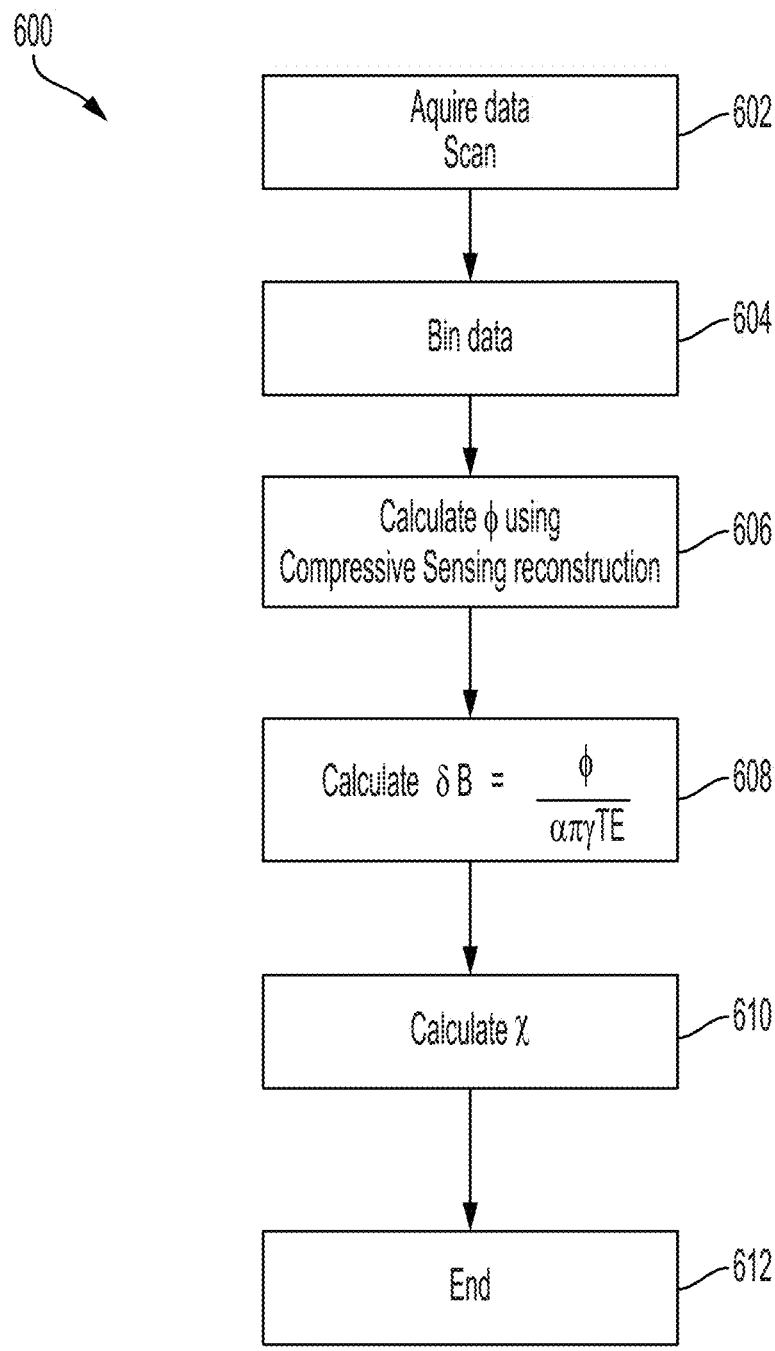
FIG. 6 illustrates an exemplary method of processing the data collected from an MRI system configured to acquire magnetic susceptibility of tissue within a patient according to examples of the disclosure.

FIG. 6 illustrates an exemplary method of processing the data collected from an MRI system configured to acquire magnetic susceptibility of tissue within a patient according to examples of the disclosure. The process 600 can begin at step 602 wherein the data is acquired from an MRI scanning procedure such as the one described above with respect to FIG. 5, using an MRI system such as the one described above with respect to FIG. 4. Once the data from the MRI scan has been acquired, the process 600 can move to step 604, wherein each data point acquired at step 602 can be placed into one or more spatial bins.

In one or more examples, a spatial bin can refer to a two dimensional (or higher) range of motion that an acquired image datapoint can be categorized. The bin is determined based on the orientation of the patient during data acquisition procedure described in FIG. 5. As described above with respect to FIG. 4, the MRI system motion can include a motion tracker 418 which can observe and record the exact position of the patient at any given moment in time. For instance in one example, the motion tracker can include a video camera that can record the patient's movement and can determine the position of the patient's body in two or more dimensions (ie., X and Y for example). When a data point is acquired, the motion tracker 418 can provide the precise orientation that the patient was in when that particular data was acquired. In one or more examples, the data point can thus have position data associated with it in two or more dimensions. For instance, using the head as an example, at any moment in time during the acquisition process, the orientation of the patient's head can be characterized in two dimensions labeled as X and Y. X can represent the degree of tilt from shoulder to shoulder while Y can represent the degree of tilt from looking down to looking up. Thus at any given moment in time during the acquisition process, the motion tracker 418 can associate an orientation of the head (using the X,Y coordinates) to each and every data point acquired at step 602.

Figure 7:
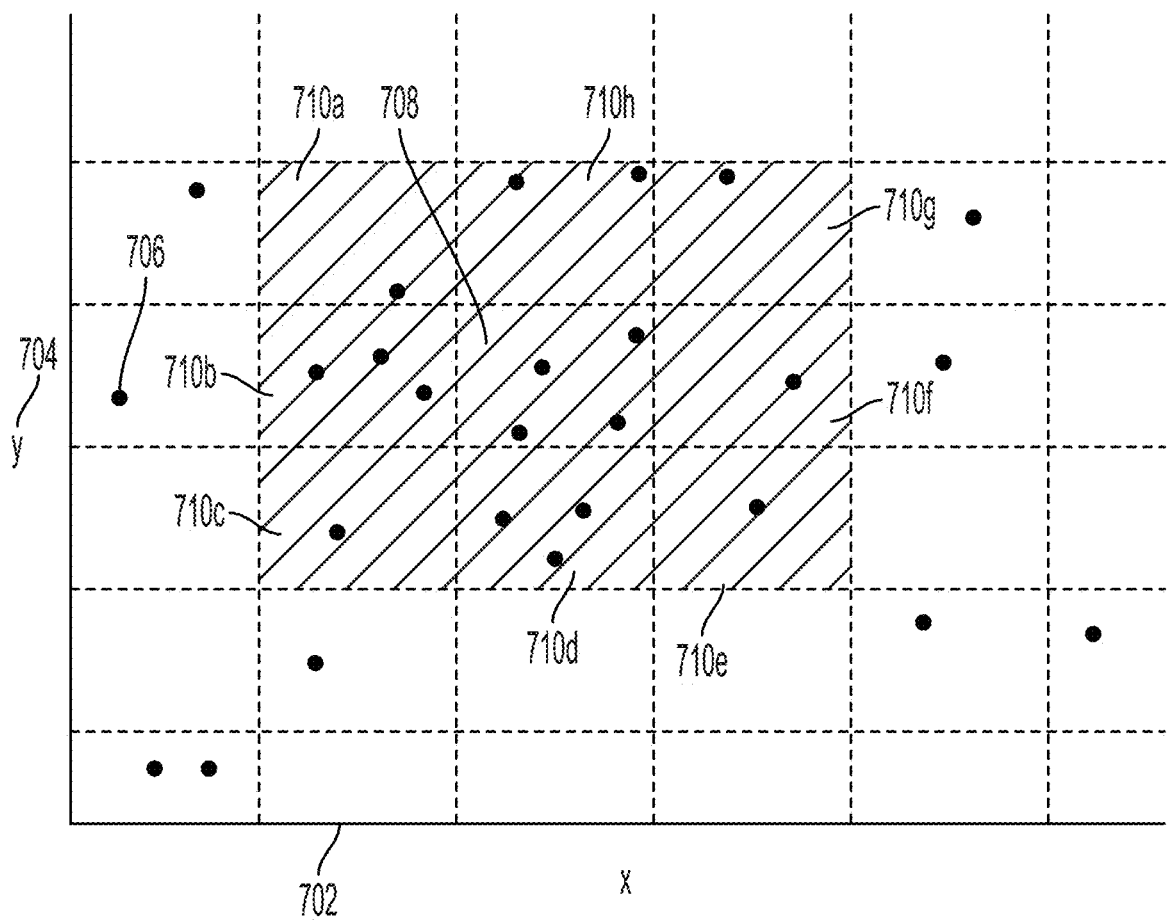
FIG. 7 illustrates an exemplary graphical representation of a binned data set according to examples of the disclosure.

In one or more examples, placing each data point into a bin can include categorizing each data point into one or more bins with each bin defined by a specific range of X and Y values. FIG. 7 illustrates an exemplary graphical representation of a binned data set according to examples of the disclosure. The example of FIG. 7 represents a visual representation of the bins described above for the purposes of explanation, however it should be understood that the bins represent a way of organizing the data acquired by the MRI scanner and thus the bins, in one or more examples, can be implemented in software rather than as a visualization. FIG. 7 illustrates a binning scheme 700, which has two dimensions 702 and 704 labeled as X and Y in the figure respectively. Each dimension 702 can be divided into one or more sections, thereby creating "bins" that represent a specific range of X values and Y values. For example, bin 708 can contain data acquired from a patient when the patient's head was positioned in a certain range of X and Y values. While the data points (represented by a dot in the figure such as the one labeled 706) may have been acquired at different moments in time, they can be placed into the same bin 708 since they were acquired at a moment when the patient's head was in the specific range of X values and Y values associated with bin 708.

In one or more examples, the size of the bins, as well as the range of the bins can be determined by the degree of movement exhibited by the patient during the data acquisition process. In one or more examples, the process for establishing the bins described above can include determining the total range of motion exhibited by the patient during the data acquisition process, and then dividing the total range of motion in each dimensions into a pre-determined number of ranges, thereby forming bins.

Returning to the example of FIG. 6, once the data acquired at step 602 has been placed into bins at step 604, the process 600 can move to step 606 wherein the phase information for each data point can be calculated using compressive sensing reconstruction. At step 606, phase images can be formed from the data at each bin, collected at step 602. However, a single bin may not have an adequate amount of data to make the dataset mathematically sufficient to solve the inverse problem. Thus, in one or more examples at step 606, in order to create a phase image at a particular bin, the data that exists in the bins adjacent to the bin in which phase information is being reconstructed can be used to create the mathematically sufficient dataset needed to create a phase image. This technique can be referred to as "compressive sensing reconstruction."

Referring back to the example of FIG. 7 to illustrate the concept of "compressive sensing reconstruction," if a phase image were being constructed from the data at bin 708 only, the amount of data may not be enough to enable the inverse problem to be adequately solved. Thus, in one or more examples, in order to obtain an adequate number of data points while minimizing errors, the process at step 606 can use the data at adjacent bins 710*a-h* to create a mathematically adequate data set so as to create a high quality phase image. Because the data found in the adjacent bins 710*a-h* were collected at positions that were spatially close to the data collected in bin 708, the data can be used to reconstruct the phase image for bin 608 while minimizing error in the formation of the phase image. General mathematical framework is given in equations 12 & 13 below.

Once a phase image has been formed for each bin at step 606, the process 600 can move to step 608, wherein the magnetic field for each bin can be calculated with respect to equation 2 described above.

Once the magnetic field is calculated at step 608, the process can move to step 610 wherein the magnetic susceptibility of the tissue being imaged can be calculated according to equations 4 and 5 described above. After calculating the magnetic susceptibility at step 610, the process can move to step 612 where it is terminated.

The compressed sensing process described above with respect can provide one method of recovering susceptibility from phase data, but other approaches to recovering susceptibility can produce the same result, such as data-driven techniques and machine learning.

The object (i.e, the tissue to be sampled) can have a default alignment to the magnetic field but can also be re-oriented with respect to the main magnetic field. For instance, let $\theta=[B_{tip}, \theta_{tilt}]$ describe the variation in orientation from the aligned position. For example, if the imaging object is a patient's head, then the patient can tip it forward and back, or tilt it from shoulder to shoulder (and combinations of those motions). In the continuous motion context, such motion is encouraged over the duration of the scan. Thus, the method can consider a rotated version of the image of interest (as obtained from coil c) from equation 1, namely, $I_c(r,\theta(t))$ where the orientation $\theta$ varies over time t. It should be noted that the spatial coordinates r can be fixed to the patient's frame of reference (as opposed to the scanner-frame of reference (as described above, which coincides with the patient-frame of reference only when $\theta=[0,0]$. In one or more examples, the spatial coordinates can also be fixed to the scanner's frame of reference.

In one or more examples, and over the duration of the scan, data can be acquired by the MRI system over time. That data collection can be modeled as discrete samples of the Fourier transform of the object, based on the solution to the Bloch equation with the scanner's gradient coils used for spatial encoding. The collected data by each coil c can be represented using equation 8 below:

$$d_c(k(t))=S(k(t))\cdot F(I_c(r,\theta(t))). \qquad \text{(equation 8)}$$

In equation 8 above, F can represent the Fourier transform, mapping $I_c(r,\theta(t))$ to its spectrum over spatial frequencies $k=[k_x, k_y, k_z]$, and $S(k(t))$ can represent a binary mask with 1 in the specific coordinates discrete spatial frequencies that were measured by the MRI system protocol (and 0 elsewhere). $d_c$ can be computed from pointwise multiplication (i.e. Hadamard product) of the mask with the spectrum. In conventional MRI, $S(k(t))$ is a uniform grid and the equation reduces to the discrete Fourier transform. Furthermore, the transform F can be modulated by the MRI receiver-coil sensitivities.

In the examples described above, $S(k(t))$ may be uniform or non-uniform samples, and furthermore they represent the scanner-frame of reference. The examples described above can employ a motion registration method (described above) to measure the orientation of the object over time, i.e. $\theta(t)$. From the motion registration, the data can be correspondingly rotated (via rotation matrix multiplication) to the patient-frame of reference. Equation 9 below, represent equation 8 above in terms of the patient's frame of reference.

$$\tilde{d}_c(\tilde{k},\theta(t))=R_{\theta(t)}\cdot d_c(k(t)) \qquad \text{(equation 9)}$$

For conciseness of notation, combine these linear operations (Fourier transform, sampling, and registration) such that $$\tilde{d}_c(\tilde{k},\theta(t))=F_{R,S}(I_c(r,\theta(t))) \qquad \text{(equation 10)}$$

Finally, the orientation-registered Fourier measurements $\tilde{d}_c$ are input into the reconstruction pipeline. The phase of $I_c$ $(r,\theta(t))$, $\phi(r,\theta(t))$, is recovered from $\tilde{d}_c(\tilde{k},\theta(t))$ according to the compressed sensing framework described above (also see equation 12 & 13).

Once the phase image is reconstructed, the resulting phase image can be used to provide a mapping of the magnetic susceptibility of the scanned object. The phase $\phi(r,\theta(t))$ matters in so much as it informs the measurement of magnetic susceptibility $\chi(r)$. $\chi$ does not depend on the orientation $\theta$. $\theta$ is varied intentionally so that incomplete measurements are overcome as described above.

The inverse problem of determining $\chi$ from $\phi(r,\theta(t))$ can be layered atop the inverse problem of recovering $\phi$ from $\tilde{d}_c$. The ultimate objective can be to recover an accurate susceptibility map from the measured data. Equation 11 below provides an exemplary relationship between the $\phi$ and $\tilde{d}$ $$\hat{\chi}(r) = \qquad \text{(equation 11)}$$
$$\underset{\chi}{\operatorname{argmin}}\left\|\tilde{d}_c(k,\theta(t)) - F_{R,S}(T_c(r)m(r)\cdot e^{-2\pi i\cdot(h(r,\theta(t))*\chi(r))\gamma TE})\right\|_c$$

A reasonable approach to solving such a layered problem is to break it down into components. For example, first recovering the phase and then performing deconvolution. One approach for recovering phase is to use compressed sensing. In this approach, the continuous object orientations $\theta(t)$ must first be discretized into bins ($\theta_n$) as described above with respect to FIGS. 5-7. Compressed sensing can be useful to generate a phase image from continuous motion data because the acquired data $\tilde{d}_c$ associated with each $\theta$ bin may be undersampled. That is, $\tilde{d}_c(k,\theta_n)$ does not include sufficient data on its own to solve the linear inverse problem for $\phi(r,\theta_n)$. Compressed sensing is a nonlinear reconstruction approach in which the data fidelity is weighed against prior assumptions (involving sparsity) to provide an optimal solution to the inverse problem. Equation 12 shows one example compressed sensing framework which can yield the desired phase (or field data)

$$\hat{m}(r), \delta B_\chi(r,\theta_n) = \underset{m,\delta B_\chi}{\operatorname{argmin}}\left\|\tilde{d}_c(k,\theta_n) - \right. \qquad \text{(equation 12)}$$
$$\left. F_{R,S}(T_c(r)m(r)\cdot e^{-2\pi i\gamma(\delta B_\chi(r,\theta_n)+\delta B_0(r,\theta_n))TE})\right\|_c^2 +$$
$$\|R(m,\phi)\|^1$$

In equation 12 above, we replaced $\phi(r,\theta_n)$ with its dependence on $\delta B_\chi(r,\theta_n)$ from Equations 2 & 3. As discussed above, the background field $\delta B_0(r,\theta_n)$ can either be estimated using existing Background Field Removal algorithms, or, alternatively, it can be jointly estimated with Equation 12 as well. The $l_2$ term (superscript 2 term) can ensure data fidelity, and the $l_1$ term (denoted by superscript 1) can incorporate sparse regularization (i.e., using data from adjacent bins to reconstruct the phase image at a particular location). In one example, $\|R(m,\phi)\|^1$ measures the total variation of the object across $\theta_n$ as denoted by equation 13 below.

$$R(m, \phi) = \sum_{\theta_n} |m(r) \cdot e^{-2\pi i \cdot \phi(r,\theta_n)} - m(r) \cdot e^{-2\pi i \cdot \phi(r,\theta_{n+1})}| \quad \text{(equation 13)}$$

In the example of equation 13, the sparse regularization can leverage that the absolute differences between adjacent $\theta_n$ bins are sparse. The mathematical assumption is that the terms of the difference are similar because m(r) does not vary with rotation, and $\theta_n$ is spatially nearby $\theta_{n+1}$. Thus the examples above exploit this similarity, and regularize the problem so that the resulting total variation is sparse (and relaxed from $l_0$ to $l_1$).

Once the reconstructed phase image is generated using the methods described above the dipole inversion step can be computed linearly—from an overdetermined system of equations, see equation 6. The dipole inversion can furthermore take into consideration the distribution of the patient motion θ(t) within each bin $\theta_n$ as described above.

The system described in FIG. 4, the method of data collection described in FIG. 5, and the method of processing the data described in FIG. 6 can overall lead to a process for generating magnetic susceptibility measurements that can significantly reduce imaging time, and improve the accuracy in magnetic susceptibility measurements.

Figure 8:
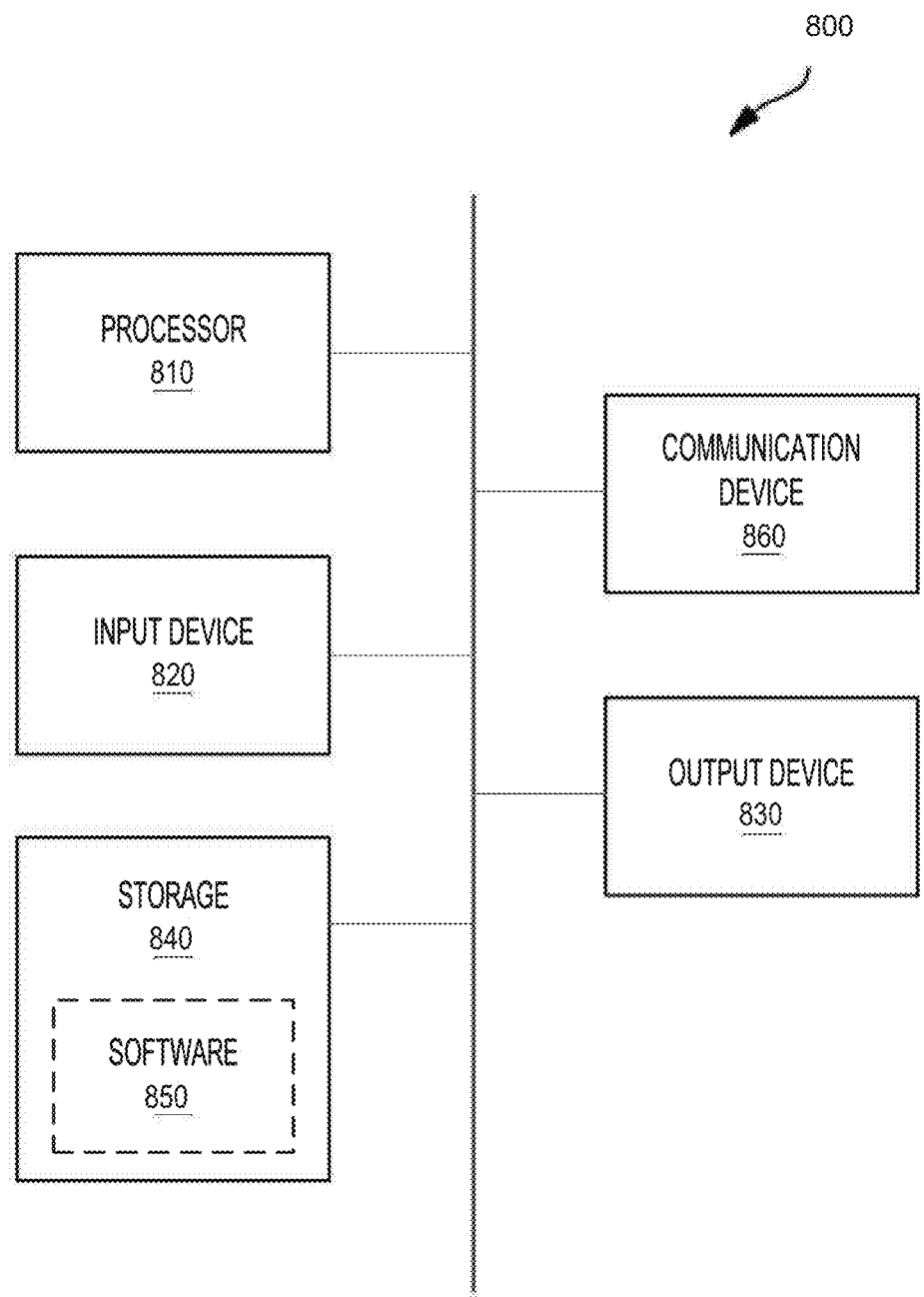
FIG. 8 illustrates an example of a computing device according to examples of the disclosure.

FIG. 8 illustrates an example of a computing device in accordance with one embodiment. Device 800 can be a host computer connected to a network. Device 800 can be a client computer or a server. As shown in FIG. 8, device 800 can be any suitable type of microprocessor-based device, such as a personal computer, workstation, server, or handheld computing device (portable electronic device), such as a phone or tablet. The device can include, for example, one or more of processors 802, input device 806, output device 808, storage 810, and communication device 804. Input device 806 and output device 808 can generally correspond to those described above and can either be connectable or integrated with the computer.

Input device 806 can be any suitable device that provides input, such as a touch screen, keyboard or keypad, mouse, or voice-recognition device. Output device 808 can be any suitable device that provides output, such as a touch screen, haptics device, or speaker.

Storage 810 can be any suitable device that provides storage, such as an electrical, magnetic, or optical memory, including a RAM, cache, hard drive, or removable storage disk. Communication device 804 can include any suitable device capable of transmitting and receiving signals over a network, such as a network interface chip or device. The components of the computer can be connected in any suitable manner, such as via a physical bus or wirelessly.

Software 812, which can be stored in storage 810 and executed by processor 802, can include, for example, the programming that embodies the functionality of the present disclosure (e.g., as embodied in the devices as described above).

Software 812 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 810, that can contain or store programming for use by or in connection with an instruction execution system, apparatus, or device.

Software 812 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate, or transport programming for use by or in connection with an instruction execution system, apparatus, or device. The transport readable medium can include, but is not limited to, an electronic, magnetic, optical, electromagnetic, or infrared wired or wireless propagation medium.

Device 800 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 800 can implement any operating system suitable for operating on the network. Software 812 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

The above description is presented to enable a person skilled in the art to make and use the disclosure and is provided in the context of a particular application and its requirements. Various modifications to the preferred embodiments will be readily apparent to those skilled in the art, and the generic principles defined herein may be applied to other embodiments and applications without departing from the spirit and scope of the disclosure. Thus, this disclosure is not intended to be limited to the embodiments shown but is to be accorded the widest scope consistent with the principles and features disclosed herein. Finally, the entire disclosure of the patents and publications referred in this application are hereby incorporated herein by reference.

What is claimed is:

1. A system for scanning for and obtaining magnetic resonance imaging (MM) phase data from a patient undergoing an MRI scan, the system comprising:
   one or more magnets;
   one or more radio frequency (RF) coils, wherein the one or more RF coils are configured to transmit and receive RF signals;
   a memory;
   one or more processors; and
   one or more programs, wherein the one or more programs are stored in the memory and configured to be executed by the one or more processors, the one or more programs when executed by the one or more processors cause the processor to:
      generate one or more magnetic fields using one or more magnets;
      transmit one or more RF signals to the patient, wherein the one or more RF signals are generated and transmitted by one or more RF coils configured to generate and transmit RF signals;
      receive a plurality RF signals from the one or more RF coils transmitted from the patient in response to the generated one or more magnetic fields and the one or more generated RF signals, wherein the received plurality of RF signals are transmitted from the patient while the patient is continuously moving during the MRI scan;
      receive data corresponding to a plurality of physical orientations of the patient and the time at which the patient was determined to be in each physical orientation of the plurality of physical orientations while continuously moving during the MRI scan;
      associate each RF signal of the received plurality RF signals with a physical orientation of the patient based on the received data;
      reconstruct a phase image associated with each of the received one or more RF signals from the patient based on the received one or more RF signals and the received data corresponding to the plurality of physical orientations of the patient and the time at which the patient was determined to be in each physical orientation of the plurality of physical orientations while continuously moving during the MRI scan, wherein reconstructing a phase image associated with the received one or more RF signals from the patient comprises:
   categorizing each received RF signal of the plurality RF signals into a bin of a plurality of bins based on the received data associated with the RF signal, wherein each bin of the plurality of bins corresponds to a range of values associated with the physical orientation of patient; and
      determining a phase information of a first RF signal categorized into a first bin of the plurality of bins based on the received RF signals categorized into the first bin and the received RF signals categorized into one or more bins adjacent to the bin, wherein the range of values associated with each adjacent bin is proximal to the range of values associated with the first bin; and
   generate a magnetic susceptibility image of the patient based on the reconstructed phase image.

2. The system of claim 1, wherein the received data corresponding to a plurality of physical orientations of the patient and the time at which the patient was determined to be in each physical orientation of the plurality of physical orientations while continuously moving during the MRI scan is received from a motion tracker.

3. The system of claim 1, wherein the one or more processors are caused to determine a magnetic susceptibility of a portion of the patient's body based on the determined phase information of the first RF signal.

4. The system of claim 3, wherein determining the magnetic susceptibility of the portion of the patient's body comprises:
   calculating a magnetic field of the portion of the patient's body based on the determined phase information of the first RF signal; and
   calculating the magnetic susceptibility of the portion of the patient's body based on the determined phase information of the first RF signal.

5. The system of claim 1, wherein the one or more processors are caused to generate an image of the portion of the patient's body based on the determined magnetic susceptibility of the portion of the patient's body.

6. The system of claim 2, wherein the motion tracker includes a camera configured to capture the orientation of a portion of the patient's body.

7. The system of claim 1, wherein a pulse sequencer is used to cause the one or more magnets to generate one or more magnetic fields, and wherein the pulse sequencer is used to cause to one or more RF coils to transmit the one or more RF signals to the patient.

8. The system of claim 7, wherein the pulse sequencer is configured to generate the one or more magnetic fields and the one or more RF signals so as to calculate the magnetic susceptibility of a portion of the patient's body.

9. The system of claim 8, wherein the pulse sequencer is configured to generate the one or more magnetic fields and the one or more RF signals based on a portion of the patient's body being scanned.

10. The system of claim 2, wherein the motion tracker collects data corresponding to the plurality of physical orientations of the patient in a first spatial dimension and a second spatial dimension.

11. The system of claim 10, wherein each bin of the plurality of bins corresponds to a range of values in the first dimension and range of values in the second dimension.

12. The system of claim 1, wherein reconstructing the phase image includes converting the received RF signals to phase information.

13. A method for scanning for and obtaining magnetic resonance imaging (MM) phase data from a patient undergoing an MRI scan, the method comprising:
   generating one or more magnetic fields using one or more magnets;
   transmitting one or more RF signals to a patient, wherein the one or more RF signals are generated and transmitted by one or more RF coils configured to generate and transmit RF signals;
   receiving a plurality RF signals from the one or more RF coils transmitted from the patient in response to the generated one or more magnetic fields and the one or more generated RF signals, wherein the received plurality of RF signals are transmitted from the patient while the patient is continuously moving during the MRI scan;
   receiving data corresponding to a plurality of physical orientations of the patient and the time at which the patient was determined to be in each physical orientation of the plurality of physical orientations while continuously moving during the MRI scan;

associating each RF signal of the received plurality RF signals with a physical orientation of the patient based on the received data;

reconstructing a phase image associated with each of the received one or more RF signals from the patient based on the received one or more RF signals and the received data corresponding to the plurality of physical orientations of the patient and the time at which the patient was determined to be in each physical orientation of the plurality of physical orientations while continuously moving during the MRI scan, wherein reconstructing a phase image associated with the received one or more RF signals from the patient comprises:

categorizing each received RF signal of the plurality RF signals into a bin of a plurality of bins based on the received data associated with the RF signal, wherein each bin of the plurality of bins corresponds to a range of values associated with the physical orientation of patient; and determining a phase information of a first RF signal categorized into a first bin of the plurality of bins based on the received RF signals categorized into the first bin and the received RF signals categorized into one or more bins adjacent to the bin, wherein the range of values associated with each adjacent bin is proximal to the range of values associated with the first bin; and generating a magnetic susceptibility image of the patient based on the reconstructed phase image.

14. The method of claim 13, wherein the received data corresponding to a plurality of physical orientations of the patient and the time at which the patient was determined to be in each physical orientation of the plurality of physical orientations while continuously moving during the MRI scan is received from a motion tracker.

15. The method of claim 13, wherein the one or more processors are caused to determine a magnetic susceptibility of a portion of the patient's body based on the determined phase information of the first RF signal.

16. The method of claim 15, wherein determining the magnetic susceptibility of the portion of the patient's body comprises:

calculating a magnetic field of the portion of the patient's body based on the determined phase information of the first RF signal; and calculating the magnetic susceptibility of the portion of the patient's body based on the determined phase information of the first RF signal.

17. The method of claim 13, wherein the method comprises generating an image of the portion of the patient's body based on the determined magnetic susceptibility of the portion of the patient's body.

18. The method of claim 14, wherein the motion tracker includes a camera configured to capture the orientation of a portion of the patient's body.

19. The method of claim 13, wherein a pulse sequencer is used to cause the one or more magnets to generate one or more magnetic fields, and wherein the pulse sequencer is used to cause to one or more RF coils to transmit the one or more RF signals to the patient.

20. The method of claim 19, wherein the pulse sequencer is configured to generate the one or more magnetic fields and the one or more RF signals so as to calculate the magnetic susceptibility of a portion of the patient's body.

21. The method of claim 20, wherein the pulse sequencer is configured to generate the one or more magnetic fields and the one or more RF signals based on a portion of the patient's body being scanned.

22. The method of claim 14, wherein the motion tracker collects data corresponding to the plurality of physical orientations of the patient in a first spatial dimension and a second spatial dimension.

23. The method of claim 22, wherein each bin of the plurality of bins corresponds to a range of values in the first dimension and range of values in the second dimension.

24. The method of claim 13, wherein reconstructing the phase image includes converting the received RF signals to phase information.

25. A non-transitory computer-readable storage medium comprising one or more programs for scanning for and obtaining magnetic resonance imaging (MRI) phase data from a patient undergoing an MRI scan, wherein the one or more programs, when executed by one or more processors, cause the one or more processors to:

generate one or more magnetic fields using one or more magnets;

transmit one or more RF signals to a patient, wherein the one or more RF signals are generated and transmitted by one or more RF coils configured to generate and transmit RF signals;

receive a plurality RF signals from the one or more RF coils transmitted from the patient in response to the generated one or more magnetic fields and the one or more generated RF signals, wherein the received plurality of RF signals are transmitted from the patient while the patient is continuously moving during the MRI scan;

receive data corresponding to a plurality of physical orientations of the patient and the time at which the patient was determined to be in each physical orientation of the plurality of physical orientations while continuously moving during the MRI scan;

associate each RF signal of the received plurality RF signals with a physical orientation of the patient based on the received data;

reconstruct a phase image associated with each of the received one or more RF signals from the patient based on the received one or more RF signals and the received data corresponding to the plurality of physical orientations of the patient and the time at which the patient was determined to be in each physical orientation of the plurality of physical orientations while continuously moving during the MRI scan, wherein reconstructing a phase image associated with the received one or more RF signals from the patient comprises:

categorizing each received RF signal of the plurality RF signals into a bin of a plurality of bins based on the received data associated with the RF signal, wherein each bin of the plurality of bins corresponds to a range of values associated with the physical orientation of patient; and determining a phase information of a first RF signal categorized into a first bin of the plurality of bins based on the received RF signals categorized into the first bin and the received RF signals categorized into one or more bins adjacent to the bin, wherein the range of values associated with each adjacent bin is proximal to the range of values associated with the first bin; and generate a magnetic susceptibility image of the patient based on the reconstructed phase image.

26. The non-transitory computer-readable storage medium of claim 25, wherein the received data corresponding to a plurality of physical orientations of the patient and the time at which the patient was determined to be in each physical orientation of the plurality of physical orientations while continuously moving during the MRI scan is received from a motion tracker.

27. The non-transitory computer-readable storage medium of claim 25, wherein the one or more processors are caused to determine a magnetic susceptibility of a portion of the patient's body based on the determined phase information of the first RF signal.

28. The non-transitory computer-readable storage medium of claim 27, wherein determining the magnetic susceptibility of the portion of the patient's body comprises:
   calculating a magnetic field of the portion of the patient's body based on the determined phase information of the first RF signal; and
   calculating the magnetic susceptibility of the portion of the patient's body based on the determined phase information of the first RF signal.

29. The non-transitory computer-readable storage medium of claim 25, wherein the method comprises generating an image of the portion of the patient's body based on the determined magnetic susceptibility of the portion of the patient's body.

30. The non-transitory computer-readable storage medium of claim 26, wherein the motion tracker includes a camera configured to capture the orientation of a portion of the patient's body.

31. The non-transitory computer-readable storage medium of claim 25, wherein a pulse sequencer is used to cause the one or more magnets to generate one or more magnetic fields, and wherein the pulse sequencer is used to cause to one or more RF coils to transmit the one or more RF signals to the patient.

32. The non-transitory computer-readable storage medium of claim 31, wherein the pulse sequencer is configured to generate the one or more magnetic fields and the one or more RF signals so as to calculate the magnetic susceptibility of a portion of the patient's body.

33. The non-transitory computer-readable storage medium of claim 32, wherein the pulse sequencer is configured to generate the one or more magnetic fields and the one or more RF signals based on a portion of the patient's body being scanned.

34. The non-transitory computer-readable storage medium of claim 26, wherein the motion tracker collects data corresponding to the plurality of physical orientations of the patient in a first spatial dimension and a second spatial dimension.

35. The non-transitory computer-readable storage medium of claim 34, wherein each bin of the plurality of bins corresponds to a range of values in the first dimension and range of values in the second dimension.

36. The method of claim 25, wherein reconstructing the phase image includes converting the received RF signals to phase information.

* * * * *